United States Patent

Alla et al.

Patent Number: 5,992,415
Date of Patent: Nov. 30, 1999

[54] FEMALE CONDOM

[76] Inventors: Ravikumar Alla; Madhusudhan Alla; Raghunatha Alla, all of 9 Webster Ct., Plainsboro, N.J. 08536

[21] Appl. No.: 09/114,265

[22] Filed: Jul. 13, 1998

[51] Int. Cl.[6] .................................................. A61F 6/06
[52] U.S. Cl. .......................... 128/830; 128/844; 128/918
[58] Field of Search ................................. 128/830–841, 128/842, 844, 918; 604/347–353

[56] References Cited

U.S. PATENT DOCUMENTS

| | | |
|---|---|---|
| 2,548,149 | 10/1951 | Fowler ..................................... 604/347 |
| 4,735,621 | 4/1988 | Hessel . |
| 5,113,873 | 5/1992 | Boarman ................................... 128/830 |
| 5,146,930 | 9/1992 | Richardson et al. . |
| 5,193,555 | 3/1993 | Richardson et al. . |
| 5,209,242 | 5/1993 | Shields .................................... 128/844 |
| 5,325,871 | 7/1994 | Reddy . |
| 5,513,654 | 5/1996 | Delson .................................... 128/844 |

*Primary Examiner*—Michael A. Brown
*Attorney, Agent, or Firm*—Reising, Ethington, Barnes, Kisselle, Learman & McCulloch, P.C.

[57] ABSTRACT

A female condom has a pouch that includes a pre-formed small diameter end for shaping a retention sponge to have a pull-out resistant rim thereon.

9 Claims, 2 Drawing Sheets

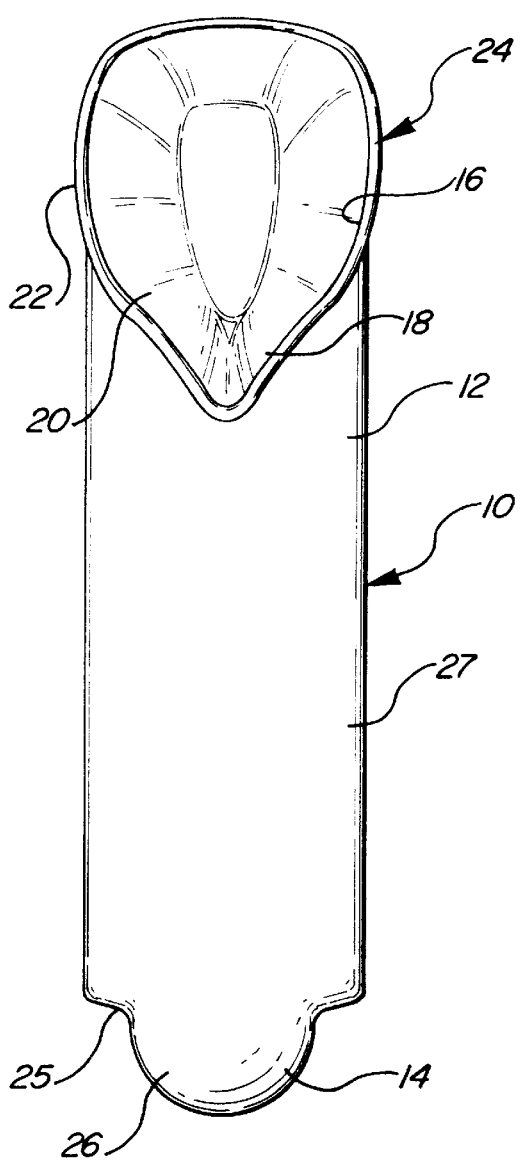
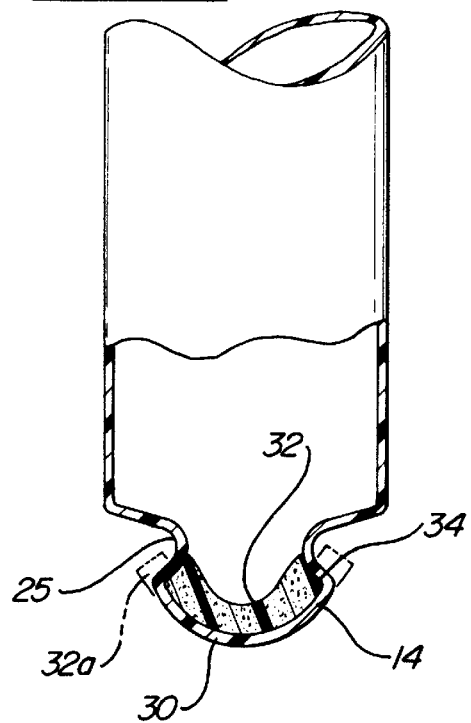
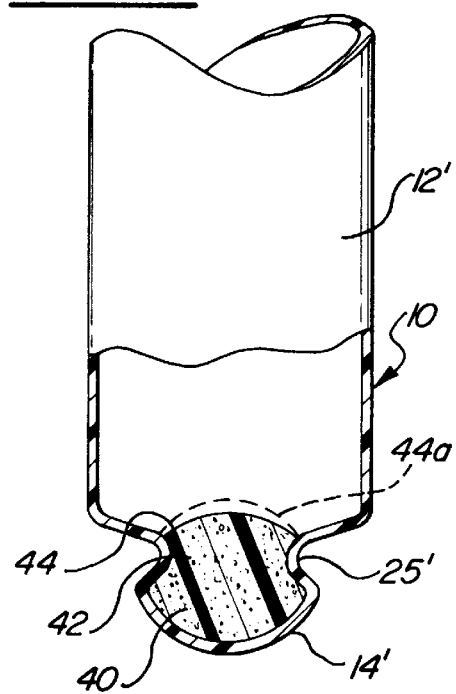

FEMALE CONDOM

FIELD OF THE INVENTION

This invention relates to prophylactic devices and more particularly to female condoms having a pouch portion and a pouch retention device.

BACKGROUND OF THE INVENTION

With the widespread prevalence of venereal disease and the growing occurrence of AIDS (acquired immune deficiency syndrome), there is an increasing need for effective means to prevent the transmission of such diseases through sexual contact and resultant exchange of bodily fluids between a user and the user's partner.

Heretofore, conventional means for preventing the transmission of such bodily fluids and exposure to such diseases because of bodily contact have included the use of condoms, jells, creams and the like.

Additionally, there have been proposals to provide female prophylactic devices which can be worn by a female prior to use and disposed of following use. It is desirable that such devices include an arrangment for securing a pouch in place to prevent withdrawal during use.

While such conventional and proposed devices are suitable for their intended purpose, it has been found that they are not totally effective for various reasons.

U.S. Pat. No. 4,735,621 likewise shows a thin walled, condom-like, tubular protective device for insertion into a vaginal canal. It includes a resilient ring on one end thereof to anchor the device in the vaginal canal.

The retention ring of the '621 patent is an integral part of the condom which requires special manufacturing tooling. Furthermore, the retention ring is configured to have a diameter corresponding to that of the pouch and a cross-sectional diameter that is small compared to the diameter of the ring. As a consequence the ring requires careful placement within the vagina so as to assure that it will fit in an interference relationship therewith to prevent the pouch from being withdrawn during coitus. Furthermore, the '621 retention ring may be oriented in a direction that will produce undesirable contact with an erected penis, i.e., causing pain during intercourse. Furthermore, the outer ring goes into the vagina during intercourse causing undesirable exposure of the users to bodily fluids.

Other female condoms have been proposed that include an internally located resilient insert element for holding the pouch portion of the female condom in place. One example is set forth in U.S. Pat. No. 5,325,871 that discloses the use of an insertable retention member that can be compressed during insertion and that will, following deployment of the female condom into its deployed position, serve both as a radially outwardly directed retention pressure device as well as a device for dispensing spermicides, fungicides or the like. U.S. Pat. No. 5,193,555, as shown in FIG. 1, requires use of an insertion tool 15. Another female condom requiring an insertion tool is shown in U.S. Pat. No. 5,146,930. In the '555 patent retention is provided by a multi-fingered insert with a central portion and a radially outwardly directed portion that springs out following tool insertion for holding the condom pouch in place. In the '930 patent retention is provided by a series of flexible protrusions that are on the outside of the pouch and that are inclined in a direction to prevent pull-out of the pouch.

While suitable for their intended purposes, such aforesaid devices have been found to lack an ease of application that will make the female condom acceptable and convenient to most users.

SUMMARY OF THE PRESENT INVENTION

In the present invention, a female condom has a pouch with a preformed closed end portion of a smaller diameter than that of the connecting pouch. The smaller diameter closed end is configured to contain a retention sponge so as to form a re-entrant rim thereon. In one embodiment, the sponge is a circular sponge of uniform thickness that is shaped to have a bowl surface for centering either an installation tool or the users finger as the pouch is inserted into the user. The shaped sponge further includes an annular rim thereon that will exert a radially outwardly directed force for shaping the retention sponge to the vaginal canal during and following installation of the female condom. Once in place, a re-entrant rim on the retention sponge is configured to resist pull-out of the pouch.

BRIEF DESCRIPTION OF THE DRAWINGS

Other advantages, features and objects of the present invention will become more apparent from the following detailed description when taken in conjunction with the appended drawings wherein:

FIG. 1 is a front elevational view of a preformed pouch on a female condom including the reduced diameter closed end of the present invention;

FIG. 2 is a perspective view of a retention sponge of the present invention prior to insertion into the pouch of FIG. 1;

FIG. 3 is a sectional view of the pouch in FIG. 1 following insertion of the retention sponge in FIG. 2;

FIG. 4 is a sectional view of another embodiment of the invention;

DETAILED DESCRIPTION OF PREFERRED EMBODIMENTS OF THE PRESENT INVENTION

Figure 5:
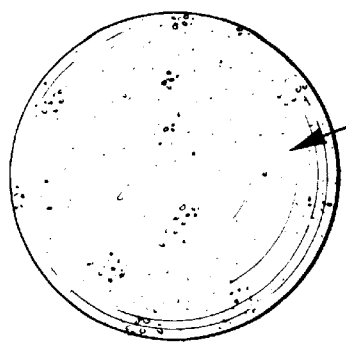
FIG. 5 is a perspective view of the retention sponge used in the embodiment of FIG. 4.

Referring now to FIG. 1, a female condom 10 is shown having preformed pouch 12 with a small diameter closed end 14 and an open end 16. A tubular outer wall 17 joins the closed end 14 with the open end 16.

A shield portion 18 has an inner surface 20 and an outer surface 22 respectively forming the front and rear panels of the condom for covering the perineum region of a user. The shield portion 18 has a frame 24 thereon, best shown in FIGS. 6–8, defining a V-shaped spring action to be discussed.

In accordance with one aspect of the present invention, the small diameter closed end 14 is preconfigured during manufacturing so as to include a reduced diameter waist portion 25 and a generally rounded closed portion 26 of slightly larger diameter than the waist portion 25 but of a reduced diameter as compared to the diameter of the main body 27 of pouch 12.

As shown in FIG. 2, a circular sponge 28 is configured to fit into the closed end 14 and to be shaped thereby in a unique manner for both ease of condom installation and retention following installation. More particularly, the circular sponge 28 has a uniform diameter and a uniform thickness of a ratio of approximately 5 to 1. Thus, in the illustrated arrangment the sponge has a diameter of 50 mm and a thickness of 10 mm. These dimensions are merely illustrative and are selected in the present application since the latex pouch 12 has a body diameter of 50 mm and the maximum diameter at the closed end is 35 mm. The ratio of the diameter and thickness of the sponge will vary as will the dimensions depending upon the size of the body of the pouch 12 and the size of the closed end thereof, but in most cases, is believed to be selected in a range between 4:1 go 6:1 in most commercial applications. The relationships of the various parts are selected such that the sponge 28 will be shaped as shown in FIG. 3 to have a middle portion 30 formed as a concave surface or bowl 32 for centering an application tool or finger during insertion of the female condom. The sponge shape and in particular the concave surface 32 will hold the applicator or inserting finger in a proper position within the pouch so that it will not slip or snag into the interior surface of the pouch during installation. Further, the sponge 28 will be shaped by the closed end 14 to adopt and be accommodated to the surrounding shape of the vaginal canal. Because of the hollow bowl configuration of the sponge 28 when inserted in the closed end 14, the sponge 28 can readily change in shape at different points within the vaginal canal during insertion so as to allow smooth comfortable installation of the female condom within a user. The sponge has a rim portion 34 thereon that will assume a reentrant shape that will resist pull out in the direction denoted by arrow P in FIG. 3. In such cases the rim portion 32 will exert a radially outwardly directed force against the walls of the vagina. Pull out forces will tend to force the rim portion into a larger diameter shape as shown in dotted lines in FIG. 3 at 32a.

In FIGS. 4 and 5 a female condom is illustrated wherein like components to those found in the embodiment of FIGS. 1–3 have the same reference numerals primed. In this embodiment the sponge is replaced by a flexible ball 40 that fits in the closed end 14' and has a sector 42 thereon pinched by the waist portion 25' to retain it in place within the pouch. The flexible ball 40 will act in the same manner as the sponge 28 to readily change in shape at different points within the vaginal canal during insertion so as to allow smooth comfortable installation of the female condom within a user. The ball will be shaped by the waist portion to have a rim portion 44 thereon that will assume a reentrant shape that will resist pull out. In such cases the rim portion 44 and the curved surface 46 of the ball 40 will exert a radially outwardly directed force against the walls of the vagina. Pull out forces will tend to force the rim portion into a larger diameter shape as shown in dotted lines in FIG. 4 at 44a.

Figure 6:
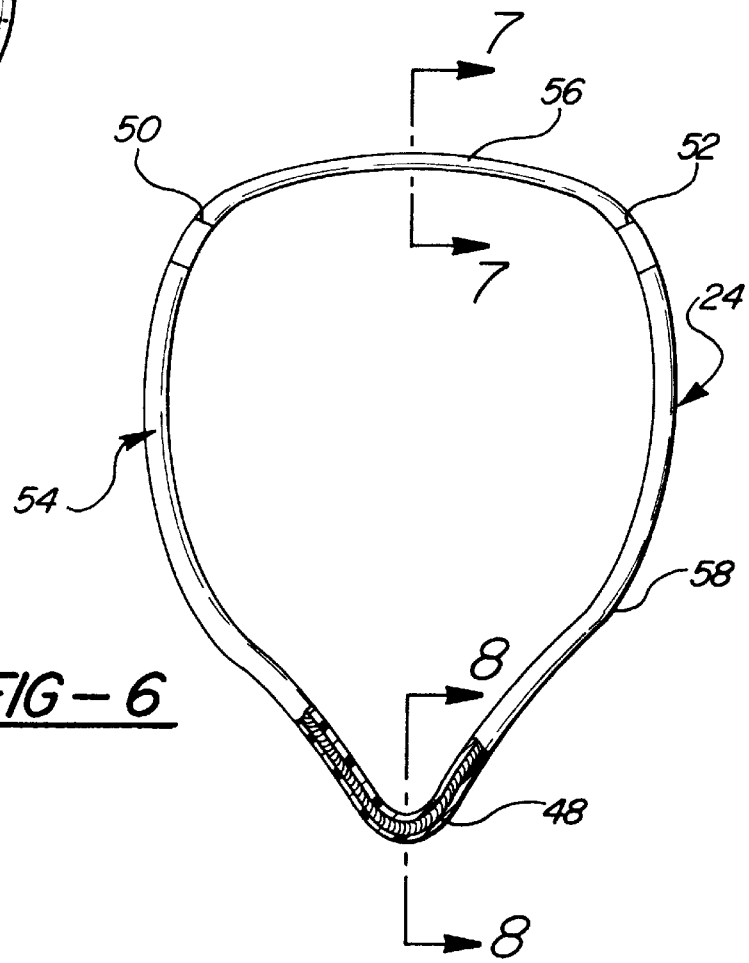
FIG. 6 is a view of a frame used to form a V-shaped spring at the inlet end of the female condom used in the embodiments of FIGS. 1–3 and FIGS. 4 and 5.
Figure 7:
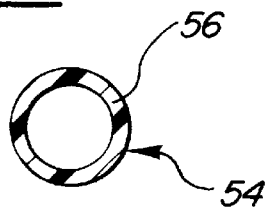
FIG. 7 is a sectional view taken along the line 7—7 of FIG. 6 looking in the direction of the arrows.
Figure 8:
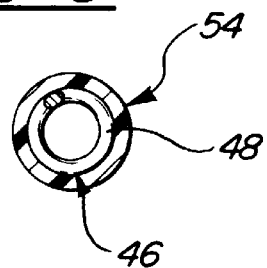
FIG. 8 is a sectional view taken along the line 8—8 of FIG. 6 looking in the direction of the arrows.

FIGS. 6–8 show a frame 24 for the open end 16 that will aid in positioning the condom on a user prior to deployment. The frame 24 is connected to the shield 18 by rolling the edges of the shield 18 thereon. The frame has a V-shaped spring 46 that allows lateral movement of the shield. The V-shaped spring 46 has an apex 48 and spaced ends 50, 52 that are biased apart to assist deployment but are easily moved together to fit the user. The spring 46 is enclosed in a tubular frame member 54 that forms a bridge 56 between the ends 50, 52. The tubular frame member is made of a suitable flexible material to easily fit over and contain the V-shaped spring 46. Open ends of the frame member are shown at the breakline 58 in FIG. 6.

The method of the present invention includes providing a circular sponge of flexible non-elastic material. Providing a female condom having an elastic pouch with a large diameter body and a smaller diameter closed end with a still smaller diameter waist portion therebetween. The method further includes inserting the sponge into the closed end of the pouch and shaping the sponge to have a reentrant rim thereon to prevent pull out. In another embodiment the method includes shaping the sponge into a hollow and flexible bowl within the closed end. Thereafter applying a force on the flexible bowl that is transmitted into a centering action for locating the female condom into a vaginal track without slippage against the interior wall of the pouch and holding the outer surface of the sponge in a convex shape for accommodating to the surrounding shape of the vaginal canal. Thereafter removing the application force and expanding the rim portion of the sponge to a reentrant position for resisting withdrawal of the pouch. Thus, the sponge accommodates for smoother insertion while providing resistance to removal to avoid pullout. The aforesaid process provides an efficient low cost anchoring technology that can be comfortably engaged by the user.

In the present invention, the female condom can be formed of material preferably made of elastic impermeable substances such as natural rubber (e.g., latex), synthetic rubber (e.g., silicone rubber), or polyurethane. Other useful materials include non-elastic substances such as various thermoplastic materials including polyethylene.

The retention sponge shown in the various embodiments of the invention can be formed of a resilient, porous material such as natural sponge material or a suitable, soft, porous sponge-like natural or synthetic material having voids. Suitable materials include natural sponge material; soft rubber open lattice material; polyurethane foam of the open cell blown type and the like that can be compressed into a compact shape and that are resiliently expandable into a retention position when deployed. The voids can be impregnated with lubricant, spermicides, fungicides, bactericides or antiviral agents that can be slowly released therefrom to protect a user as desired.

While the best mode for carrying out the invention has herein been described in detail, those familiar with the art to which this invention relates will recognize various alternative designs and embodiments for practicing the invention.

What is claimed is:

1. A female condom having a pouch with a closed end and a tubular portion insertable into a vagina and the pouch further including an open end thereon connected to a shield portion secured to the pouch and wherein the shield portion has an outer surface and an inner surface for covering the perineum of a user and having a retention sponge within the pouch characterized by:

said pouch having a main body of a first diameter; a preconfigured end formed on said main body including a reduced diameter waist portion and a generally rounded closed portion; said closed portion having a diameter larger than the diameter of said waist portion and said closed portion having a diameter smaller than said main body said retention sponge is;

a single sponge of flexible material located within said closed portion; said single sponge shaped by said closed portion and said waist portion to assume a reentrant shape to prevent pullout of the pouch.

2. The female condom of claim 1 further characterized by said sponge being a circular sponge including a rim and said circular sponge having a bowl formed therein when shaped by said closed portion for applying a centering force on said sponge during insertion of the female condom and said rim portion assuming a reentrant shape that will resist pull out.

3. The female condom of claim 2 further characterized by said circular sponge having a uniform diameter and a uniform thickness prior to shaping by said closed portion.

4. The female condom of claim 2 further characterized by said circular sponge having a diameter to thickness ratio between 4:1 and 6:1.

5. The female condom of claim 4 wherein said V-shaped spring portion has two spaced apart ends thereon and a first tubular member covering said V-shaped spring portion and configured to form said bridge portion between said two spaced apart ends.

6. The female condom of claim 1 wherein said sponge is a round ball.

7. The female condom of claim 1 having a shield at the inlet end thereof including a frame; said frame having a V-shaped spring portion at one end thereof and having a bridge portion at the opposite end thereof.

8. A method for installing a female condom comprising the steps of: providing a single circular sponge of flexible material; providing a female condom having an elastic pouch with a main body of a first diameter; a preconfigured end formed on said main body including a reduced diameter waist portion and a generally rounded closed portion; said closed portion having a diameter larger than the diameter of said waist portion and said closed portion having a diameter smaller than said main body; inserting the single sponge into the closed end of the pouch and shaping the sponge between said waist portion and said closed portion into a reentrant shape within the closed end.

9. The method of claim 8 including the steps of providing the single sponge to have a rim portion; shaping the sponge to have a bowl and applying an application force on the bowl that is transmitted into a centering action for locating the female condom into a vaginal track without slippage against the interior wall of the pouch; and holding the outer surface of the sponge in a convex shape for accommodating to the surrounding shape of the vaginal canal; thereafter removing the application force and expanding the rim portion of the sponge to a reentrant shape for resisting withdrawal of the pouch.

* * * * *